United States Patent [19]

Sekerich

[11] 4,003,536

[45] Jan. 18, 1977

[54] INTRAVENOUS BOTTLE SUPPORT ARM

[75] Inventor: Michael Sekerich, Spring Valley, N.Y.

[73] Assignee: Grant Hardware Company, West Nyack, N.Y.

[22] Filed: June 27, 1975

[21] Appl. No.: 590,925

Related U.S. Application Data

[63] Continuation of Ser. No. 359,270, May 11, 1973, abandoned.

[52] U.S. Cl. .............................................. 248/280
[51] Int. Cl.² ...................................... F16M 13/00
[58] Field of Search .......... 248/280, 281, 291, 293; 403/92, 93, 98, 146, 157

[56] References Cited

UNITED STATES PATENTS

| 213,775 | 4/1879 | Redman | 248/281 |
|---|---|---|---|
| 218,210 | 8/1879 | Alling et al. | 248/281 |
| 481,408 | 8/1892 | Manley | 248/291 X |
| 586,415 | 7/1897 | Biddle | 248/281 |
| 806,790 | 12/1905 | Foersterling | 248/281 |
| 1,070,525 | 8/1913 | Pieper | 248/281 |
| 1,189,754 | 7/1916 | Trenaman | 248/281 |
| 1,568,086 | 1/1926 | Pieper | 403/93 X |
| 1,644,661 | 10/1927 | Aufenast | 248/292 X |
| 2,131,693 | 9/1938 | Smith | 248/281 X |
| 2,176,629 | 10/1939 | Juilfs | 403/146 |
| 3,282,267 | 11/1966 | Eidus | 248/281 X |
| 3,774,873 | 11/1973 | Krogsrud | 248/280 |

FOREIGN PATENTS OR APPLICATIONS

| 11,280 | 3/1900 | United Kingdom | 403/93 |

Primary Examiner—William H. Schultz
Attorney, Agent, or Firm—Howard C. Miskin

[57] ABSTRACT

An intravenous bottle support includes a linear horizontal linkage formed of a pair of parallelogram linkages depending and diverging from a common upper pivot plate, corresponding arms of each parallelogram linkage being linked to a vertically movable member. The proximate end of the linkage is supported by a wall mounting bracket for frictionally restrained swinging about a vertical axis and the distal end of the linkage carries an upwardly directed bottle support arm which is angularly adjustable about a horizontal transverse axis and is releasably locked at a preselected angle.

7 Claims, 6 Drawing Figures

U.S. Patent   Jan. 18, 1977   Sheet 1 of 2   4,003,536
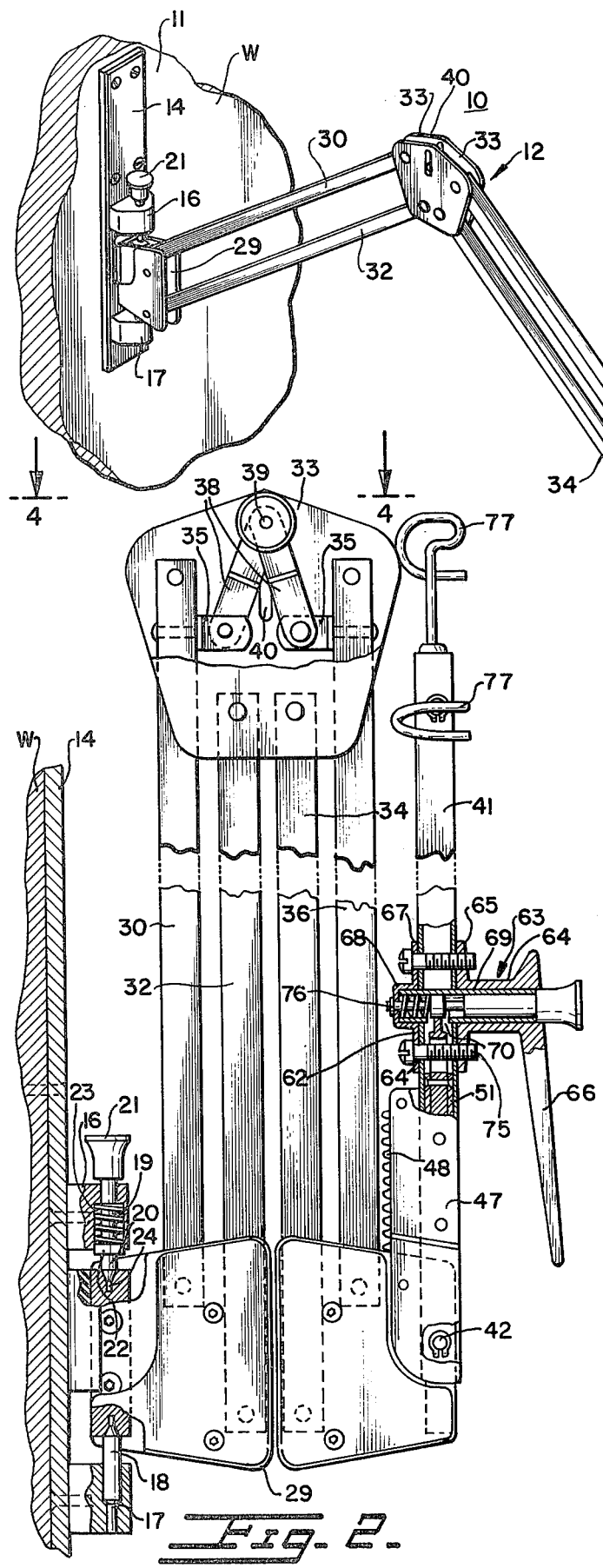
Fig. 1.
Fig. 2.
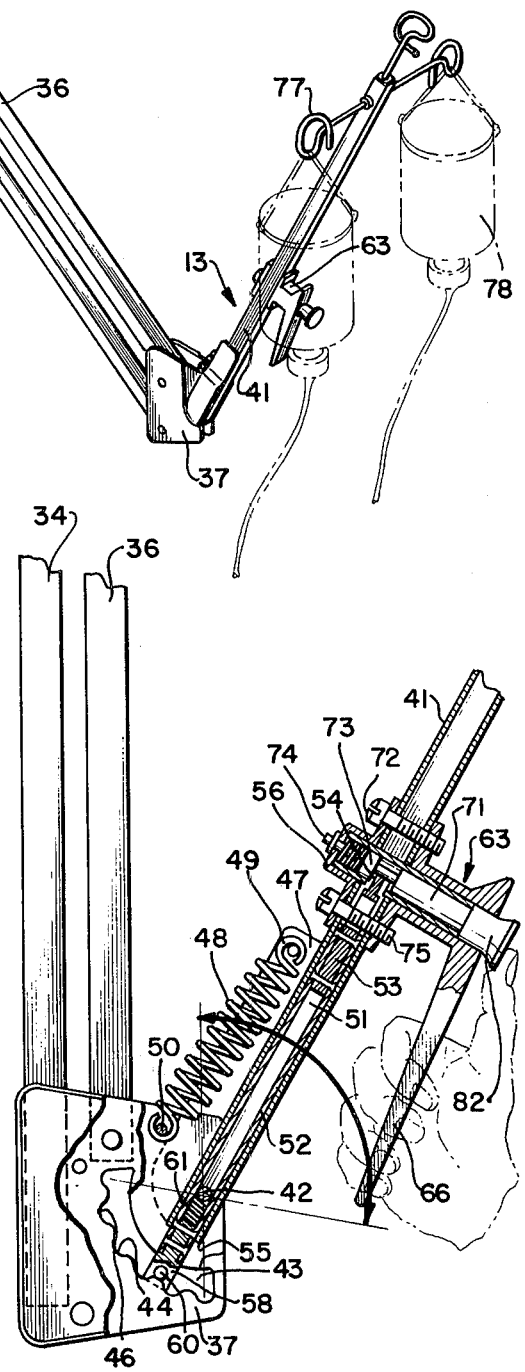
Fig. 3.

INTRAVENOUS BOTTLE SUPPORT ARM

This is a continuation of application Ser. No. 359,270 filed May 11, 1973, now abandoned.

BACKGROUND OF THE INVENTION

The present invention relates generally to improvements in adjustable supports and it relates more particularly to an improved collapsible and adjustable support for intravenous solution bottles.

There are many medical and surgical procedures which require the support of a vessel or other device above the level of a patient. Thus, it is common to intravenously feed a patient during or following surgery or under many other circumstances. To facilitate such intravenous feeding, a bottle containing an intravenous solution is supported by means of a bail in an inverted position at a certain height above the patient to provide a suitable head to the solution. The devices most commonly employed for supporting the intravenous solution bottle consists of roller supported stand or a bedpost mounted tree both of which devices possess numerous drawbacks and disadvantages. They are awkward and inconvenient, often interfere with ready access to the patient and of difficult and limited adjustment and otherwise leave much to be desired.

SUMMARY OF THE INVENTION

It is accordingly a principal object of the present invention to provide an improved support device.

Another object of the present invention is to provide an improved adjustable support for intravenous solution bottles.

Still another object of the present invention is to provide a wall mounted support for intravenous solution bottles which is contractable to a compact state and readily extendable and universally adjustable.

A further object of the present invention is to provide a device of the above nature characterized by its ruggedness, reliability, great convenience, ease of use, and high versatility and adaptability.

The above and other objects of the present invention will become apparent from a reading of the following description taken in conjunction with the accompanying drawings which illustrate a preferred embodiment thereof.

In a sense the present invention contemplates the provision of a support device comprising a wall mounting bracket for swining about a vertical axis and having a distal end linearly horizontally movable between a retracted position adjacent to the proximate end and an extended position remote from the proximate end, a support arm mounted to the linkage distal end and extending upwardly or outwardly and being angularly adjustable about a horizontal axis, and bottle support members located near the free end of the support arm.

In its preferred form the extension linkage consists of a pair of similar parallelogram linkages, the arms of which are pivoted at their upper ends to a common pivot plate having a vertical guide slot slidably engaged by a follower pin which is link-coupled to similar points on corresponding arms of each parallelogram linkage. The arms of the inner parallelogram linkage are pivoted at their outer ends to a pivot plate mounted on a bearing block having vertically aligned sockets releasably engaged by vertically aligned pivot pins mounted on the wall bracket. A resilient friction pad is located on the bearing block and frictionally engages the face of the bracket base plate. The support arm is pivoted to a quadrant plate to which the outer parallelogram arms are pivoted at their outer ends and is spring biased to a vertical position. A quadrant slot with an undulate edge is formed in the quadrant plate and a spring loaded follower carried by the support arm engages the undulate edge. The support arm is locked in a preselected angular position by releaseably locking the follower pin from movement radially inwardly from the quadrant edge.

The improved support device is reliable, rugged and convenient, easily universally adjustable, contractable to a very compact condition and is highly versatile and adaptable.

BRIEF DESCRIPTION OF THE DRAWINGS

FIG. 1 is a front perspective view of an intravenous feed bottle support device embodying the present invention shown in an extended position;

FIG. 2 is a front elevational view thereof partially fragmented and in section and shown in a fully retracted condition;

FIG. 3 is a fragmented front elevational view of the outer end thereof showing the adjustment of the bottle support arm;

DESCRIPTION OF THE PREFERRED EMBODIMENT

Figure 4:
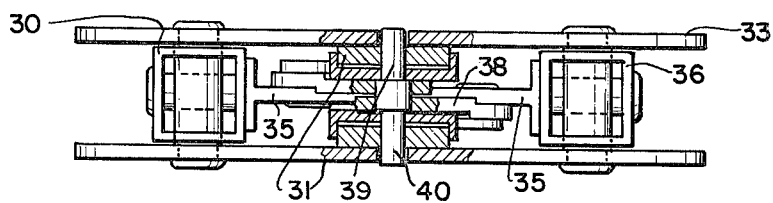
FIG. 4 is a sectional view taken along line 4—4 in FIG. 2.
Figure 5:
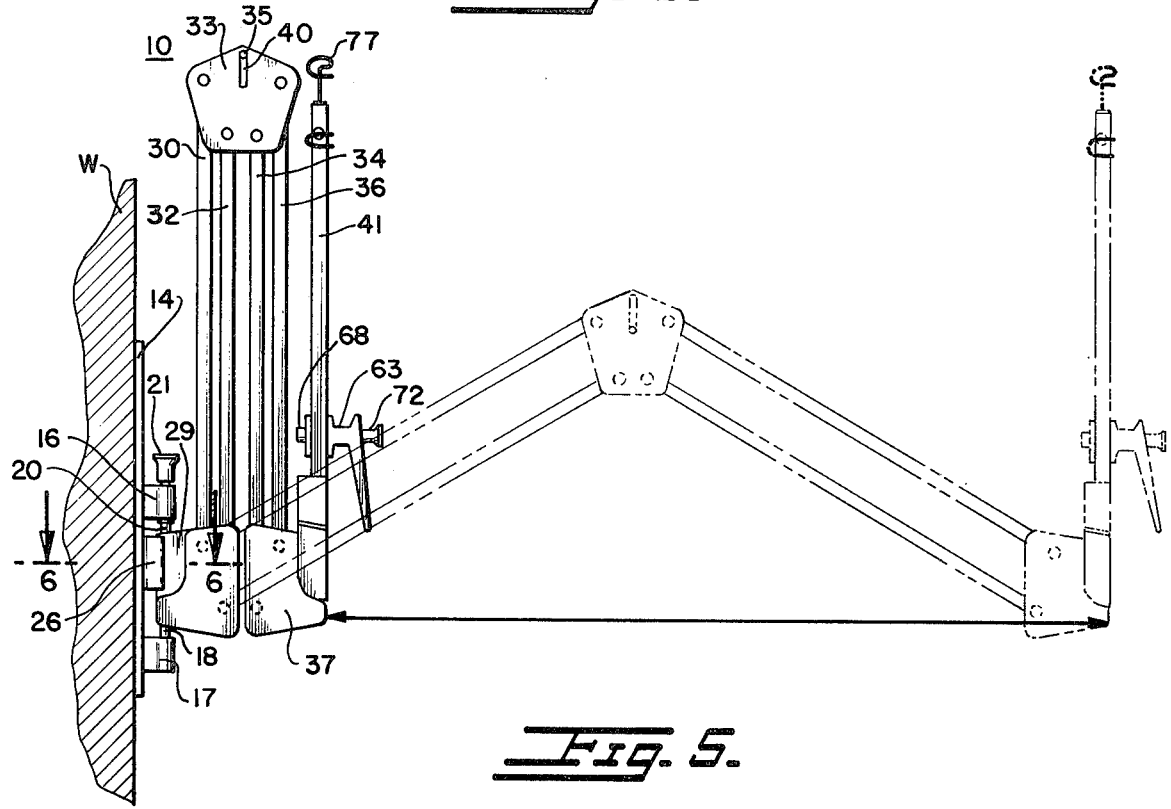
FIG. 5 is a side elevational view thereof showing the support device by full and broken line in contracted and extended positions respectively.
Figure 6:
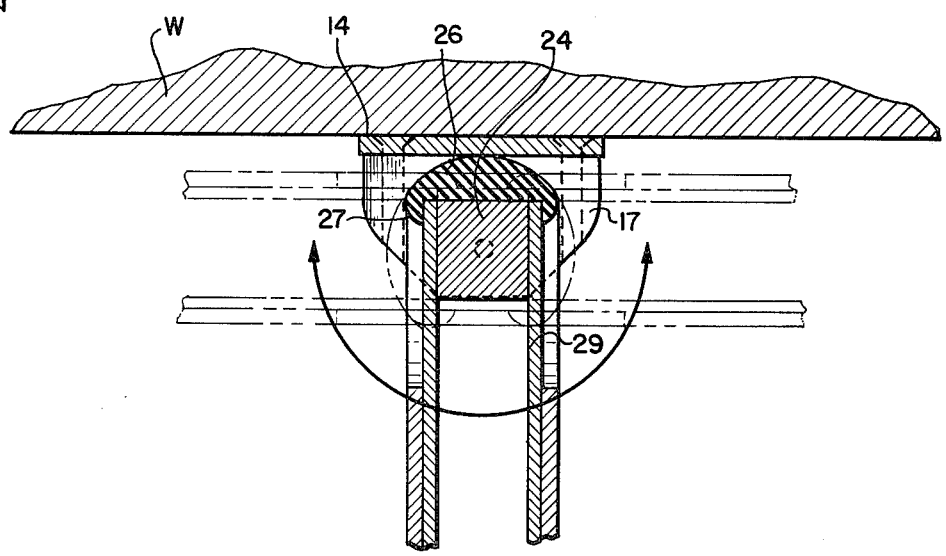
FIG. 6 is an enlarged sectional view taken along line 6—6 in FIG. 5.

Referring now to the drawings which illustrate a preferred embodiment of the present invention, the reference numeral 10 generally designates the improved extendable support device 10 which is mounted on a suitable wall "W" proximate and above a table or bed upon which the patient lies, who is to be intravenously fed. The support device 10 includes a wall mounting bracket 11, which supports for swinging about a vertical axis, a horizontally linearly extendable extension assembly or section 12, at the extendable outer end of which is mounted for adjustment about a horizontal transverse axis, a support arm section 13.

The mounting bracket 11 includes rectangular vertical base plate 14 secured to wall W by mounting screws and having mounted on its front face a pair of vertically spaced upper and lower blocks 16 and 17 respectively. A first pivot pin 18 is fixed in a vertical bore in block 17 and projects vertically therefrom. A socket 19 is formed in the underface of block 16 coaxial with pin 18 and a depending vertical pivot pin 20, coaxial with pivot pin 18 slidably registers with and extends through socket 20 and a coaxial bore of reduced diameter beyond the top block 16 and terminates in a knob 12. A peripheral flange 22 affixed to pivot pin 20 slidably engages the lower part of socket 19 and a helical compression spring 23 is entrapped between the base of socket 19 and flange 22 to resiliently urge pivot pin 20 to its lowermost position.

A swing block 24 has vertically aligned bearing sockets formed in its top and bottom faces which mate and rotatably engage the free confronting ends of pivot pins 18 and 20. Affixed to the rear face of swing block 24 and extending for a major part of its length and projecting rearwardly therefrom is a friction pad 26 formed of any suitable resilient friction material such as polyurethane or the like. The rear face of friction pad 26 is cylindrical and coaxial with the rotational axis of block 24 and bears on the face of base plate 14 to frictionally restrain the free rotation of block 24. The side borders 27 of friction pad 26 embrace the side faces of block 24 and the outside faces of borders 27 are inwardly recessed so as to be spaced from base plate 14 when block 24 is swung to a position with the side faces of block 24 being parallel to base plate 14.

Secured to and sandwiching swing block 24 are a pair of parallel forwardly projecting pivot plates which may be provided with superimposed cover plates. A pair of upper rear and lower forward, parallel, similar parallelogram link arms 30 and 32 respectively and their inner ends projecting between plates 29 and pivoted thereto at upper rear and lower forward points for swinging about corresponding horizontal axes, the arms 30 and 32 being tubular and of square transverse cross section. The upper ends of the arms 30 and 32 are sandwiched between and pivotly connected to a pair of transversely spaced parallel intermediate pivot plates 33 for swinging about horizontal axes relatively vertically and longitudinally offset like the axes of rotation of the lower ends of arms 30 and 32 to provide a parallelogram linkage.

A second pair of parallelogram linkage arms 34 and 36 similar in shape, dimensions and relationship to link arms 30 and 32 and symmetrical thereto have their upper ends sandwiched between and pivoted to plates 33 for swinging about axes forward and at the levels of the axes of swing of the upper ends of link arms 30 and 32. The lower ends of link arms 34 and 36 extend between and are pivoted to the rear sections of a pair of transversely spaced parallel quadrant plates 37 to define second parallelogram linkages therewith similar and symmetrical to the parallelogram linkage including arms 30 and 32.

Secured to the confronting faces of link arms 30 and 36 between their upper pivot points and the upper ends of link arms 32 and 34 are a pair of arms 35 which are directed toward each other and swingable with corresponding link arms 30 and 36. Pivotly connected to the free ends of arms 35 are similar links 38 which converge upwardly and pivotly engage the enlarged medial section of a transverse pin 39 whose outer sections slidably engage a pair of opposite vertical slots 40 medially formed in the upper sections of intermediate pivot plates 33. Friction washer and washer assemblies 31 engage the pin 39 and are sandwiched between the confronting faces of pivot plates 33 and links 38. The linkage between the two parallelogram linkages by way of arms 35, links 38, pin 39 and slots 40 couple the parallelogram linkages so that the quadrant plates 37 are restricted to movement along a horizontal linear path relative to the pivot plates 29 and such movement may be easily effected by pulling or pushing in the plates 37 to effect the expansion or contraction respectively of the double parallelogram linkage 12.

The support arm section 13 includes a tubular support arm 41 of square transverse cross section swingably connected at its inner lower end between quadrant plates 37 proximate their medial front borders by means of a suitable pivot pin 42 journalled between plates 37. Formed in each of the plates 37 coaxial with pin 42 are a pair of opposite similar quadrant slots 43 have outer curved undulate edges providing regularly peripherally spaced valleys or recesses 46. The lower section of support arm 41 is sandwiched between a pair of laterally spaced longitudinal plates 47 which are secured to the side walls of support arm 41 and project shortly rearwardly thereof. A helical tension spring 48 has a hooked upper end engaging a pin 49 mounted between the upper rear corners of plates 47 and a hooked lower end engaging a pin 50 mounted between the upper borders of plate 37 to resiliently bias support arm 41 counter-clockwise to an upright vertical retracted position as shown in FIG. 2, with the spring 48 nesting between the rear borders of plates 47. A lock assembly 51 longitudinally slidably telescopes the lower part of support arm 41 and includes a pair of similar front and rear link strips 52 slidably engaging the inside faces of the front and rear walls of support arm 41. Sandwiched between and secured to the upper sections of strips 52 is a cam block 53 terminating at its top above strips 52 in an axial finger 54, a forwardly rearwardly extending longitudinal slot 56 being formed in block 53 directly below finger 54. A yoke 58 is secured to the lower ends of strips 52 by means of a tongue 59 extending from yoke 58 to between strips 52 to which it is secured. A transverse follower pin 60 is supported by the yoke 58 and slidably engages the quadrant edge 44 and a helical compression spring 61 is entrapped between pivot pin 42 and the confronting face of tongue 57 to resiliently urge the assembly 51 to an extended position from support arm 41.

Mounted on the front face of support arm 41 directly above the assembly 51 is a handle 63 which includes a hollow tubular shank 64 terminating at its front in flanges 65 engaging the front face of support arm 41 and terminating at its rear in a depending hand grip 66. A housing member 67 is located in the rear face of support arm 41 and includes a centrally apertured cap section 68 coaxial with shank 64 and a pair of opposite flanges overlying the rear face of support arm 41, the housing 67 and handle 63 being received in position by screws 75 registering with aligned openings in flanges 62 and the walls of arm 41 and engaging tapped openings in flanges 65. A tubular bushing 69 registers with the cap 68 and the bore in shank 64 and extends from a point inwardly of the outer end of shank 64 through openings in the walls of support arm 41 into cap 68 and is provided in its bottom wall with an opening 70 through which finger 54 projects.

A cylindrical plunger 71 slidably telescopes the bushing 69 and terminates at its outer end in a finger knob projecting beyond the outer face of handle 63. A peripheral groove 72 is formed in plunger 71 and is followed by a cylindrical locking section 73 from which projects a coaxial shaft 74 of reduced diameter which slidably engages an opening in the end wall of cap 68. A helical compression spring 76 is entrapped between the confronting faces of cap 68 and cylindrical section 73 to resiliently urge plunger 71 to its outermost position as limited by a stop washer mounted on the free outer end of shaft 74. It should be noted that when the plunger 71 is in its fully retracted position under the influence of spring 76 cylindrical section 73 registers with finger 54 as shown in FIG. 2, and upon depression of plunger 71 by pressing on knob 82, the groove 72 registers with finger 54 thereby permitting the slide assembly 51 to raise to a position where follower pin 60 can clear the ridges of undulate edge 44.

Suitably mounted to the free end of support arm 41 are a plurality of looped hook members 77 of known construction for releasably engaging the support balls of depending inverted intravenous fluid bottles. The hook members extend laterally and axially from support arm 41.

The use and operation of the improved support device 10 is clear from the above, the device 10 being mounted by means of the base plate 14 on a wall W proximate a bed, chair, table, or other patient carrying device. In its rest condition, as shown, the arm 41 is vertically upright, and the linkage assembly 12 is in its retracted condition as shown in FIG. 2 and turned to lie flat against wall W. To use the support, support device 10 is pivoted about the mounting bracket 11 and pulled by the handle 63 to the desired extension of linkage assembly 12. Thereafter, the knob 82 is depressed and the arm 41 is adjusted to the desired increment angle with the follower pin 60 registering with a selected quadrant valley 46, the swinging of arm 41 being permitted because of the release of slide assembly 51 for vertical movement in arm 41. The knob 82 is then released to bring cylinder 73 into registry with finger 54 and prevent the raising of follower pin 60 with slide assembly 51 thereby locking arm 41 in its present position. The friction pad 26 inhibits the swinging of device 10 about support bracket 11. One or more intravenous feed bottles 78 may be suspended from hook members 77.

To return the device 10 to its collapsed condition, knob 82 is depressed to permit spring 48 to return arm 41 to its vertical position, the linkage assembly is then pushed to its collapsed condition and swing to lie along wall W, where its free swinging is prevented.

While there has been described and illustrated a preferred embodiment of the present invention, it is apparent that numerous alterations, omissions and additions may be made without departing from the spirit thereof.

What is claimed is:

1. A support device comprising a wall mounting bracket, a horizontal linear extension linkage supported at its proximate end in said wall mounting bracket for swinging about a vertical axis and having a distal end restricted to a linear horizontal movement between a retracted position adjacent said proximate end and an extended position remote from said proximate end, said linkage comprising a pair of end to end proximate and distal parallelogram linkages, means connecting said parallelogram linkages at their adjacent upper ends, said parallelogram linkages depending from said connecting means and means coupling said parallelogram linkages to restrict the parallelogram linkages to similar corresponding opposite movements, said parallelogram linkages being in vertical juxtaposition with said connecting means being uppermost when said extension linkage is fully retracted, a support arm mounted to the bottom distal end of said distal parallelogram linkage and extending upwardly therefrom and being angularly adjustable about a horizontal axis transverse to the direction of extension of said extension linkage proximate to the inner end of said arm and independently of the extended position of said horizontal linear extension linkage, said arm being juxtapositioned to said distal parallelogram linkage when said extension linkage is fully retracted and said arm is adjusted to a fully retracted vertical position, spring means resiliently urging said support arm to a vertical position, means on said support arm releasably locking said support arm in a preselected angular position, said locking means comprises a vertical plate mounted at said linkage distal end and having an arcuate indexing edge coaxial with said support arm horizontal adjustment axis and a locking element mounted on and swingable with said support arm and selectively adjustable into and out of locked engagement with said indexing edge, and a bottle support member located on said support arm proximate its outer end.

2. The support device of claim 1 wherein said indexing edge is of undulate configuration and comprising spring means urging said locking element toward said indexing edge and means for releasbly locking said element against movement in a direction away from said indexing edge.

3. The support device of claim 1 including means frictionally restraining the swinging of said extension linkage about said vertical axis.

4. The support device of claim 1 wherein said connecting means comprises a vertical pivot plate and each parallelogram linkage include a pair of parallel arms pivoted at their upper ends to spaced points on said pivot plate.

5. The support device of claim 4 wherein said pivot plate has a vertical medial guide slot formed therein and said coupling means comprises a follower member slidably engaging said guide slot and a pair of links swingably engaging and diverging from said follower member and pivotly coupled at their free ends to similarly located points on corresponding arms of said parallelogram linkages.

6. The support device of claim 1 including a bearing block positioned in the distal end of said linkage and having vertically aligned upper and lower bearing sockets, said wall mounting bracket including a pair of vertical coaxial pivot pins engaging said sockets.

7. The support device of claim 6 wherein one of said pivot pins is axially movable and spring means biasing said movable pivot pin toward the other pivot pin.

* * * * *